United States Patent
Celewicz et al.

(10) Patent No.: US 9,605,017 B2
(45) Date of Patent: *Mar. 28, 2017

(54) 2′, 5′-DIDEOXY-5-FLUOROURIDINE DERIVATIVES HAVING CYTOTOXIC ACTIVITY, A PROCESS FOR THE MANUFACTURE THEREOF AND APPLICATION THEREOF

(71) Applicant: ADAM MICKIEWICZ UNIVERSITY, Poznań (PL)

(72) Inventors: Lech Celewicz, Poznań (PL); Karol Kacprzak, Pecna (PL); Marta Lewandowska, Śrem (PL); Piotr Ruszkowski, Suchy Las (PL); Natalia Kleczewska, Poznań (PL)

(73) Assignee: ADAM MICKIEWICZ UNIVERSITY, Poznań (PL)

( * ) Notice: Subject to any disclaimer, the term of this patent is extended or adjusted under 35 U.S.C. 154(b) by 97 days.

This patent is subject to a terminal disclaimer.

(21) Appl. No.: 14/413,618

(22) PCT Filed: Mar. 4, 2014

(86) PCT No.: PCT/PL2014/050010
§ 371 (c)(1),
(2) Date: Jan. 8, 2015

(87) PCT Pub. No.: WO2015/041550
PCT Pub. Date: Mar. 26, 2015

(65) Prior Publication Data
US 2016/0244473 A1 Aug. 25, 2016

(30) Foreign Application Priority Data
Feb. 12, 2014 (PL) .......................... 407153

(51) Int. Cl.
| | | |
|---|---|---|
| *A01N 43/04* | (2006.01) | |
| *A61K 31/70* | (2006.01) | |
| *C07H 19/06* | (2006.01) | |
| *A61K 31/7072* | (2006.01) | |
| *A61K 31/7068* | (2006.01) | |
| *A61K 31/7064* | (2006.01) | |
| *A61K 31/706* | (2006.01) | |

(52) U.S. Cl.
CPC ............ *C07H 19/06* (2013.01); *A61K 31/706* (2013.01); *A61K 31/7064* (2013.01); *A61K 31/7068* (2013.01); *A61K 31/7072* (2013.01)

(58) Field of Classification Search
None
See application file for complete search history.

(56) References Cited

FOREIGN PATENT DOCUMENTS

EP 1 477 488 B1 8/2009

OTHER PUBLICATIONS

Efthymiou et al. Molecules (2012), vol. 17, pp. 12665-12703.*
Colla et al., "Synthesis and biological activity of 3′-azido- and 3′-amino substituted nucleotide analogs", *Eur. J. Med. Chem.*, 1985, 20, 4, 295-301.
Lin et al., "Synthesis and Biological Activity of Various 3′Azido and 3′-Amino Analogues of 5-Substituted Pyrimidine Deoxyribonucleosides", *J. Med. Chem.*, 1983, 26, 1691-1696.
Vichai et al., "Sulforhodamine B colorimetric assay for cytotoxicity screening", *Nature Protocols*, 2006, 1,3, 1112-1116.
Grabowski et al., "Properties and Architecture of Drugs and Natural Products Revisited", *Curr. Chem. Biol.*, 2007, 1, 115-127.
Vistoli et al., "Assessing drug-likeness—what are we missing?", *Drug Discov. Today* 2008, 13, 7/8, 285-294.
Mauri et al., "Dragon Software: An Easy Approach to Molecular Descriptor Calculations", *MATCH Commun. Math. Comput. Chem.*, 2006, 56, 237-248.
Kacprzak et al., "An Improved Synthesis of 10,11-Didehydro *Cinchona* Alkaloids", Chirality, 2008, 20, 441-445.
Baraniak et al., "Synthesis of 3′azido-3′deoxythymidine (AZT)-*Cinchona* alkaloid conjugates via click chemistry: Toward novel fluorescent markers and cytostatic agents", *Bioorganic & Medicinal Chem. Letters*, 2011, 21, 2, 723-726.
Kumar et al., "Phenyl 1,2,3-Triazole-Thymidine Ligands Stabilize G-Quadruplex DNA, Inhibit DNA Synthesis and Potentially Reduce Tumor Cell Proliferation over 3′-Azido Deoxythymidine", PLOS One, 2013, 8, 8, e70798, 1-12.

(Continued)

*Primary Examiner* — Patrick Lewis
(74) *Attorney, Agent, or Firm* — Oliff PLC

(57) ABSTRACT

The subject matter of the invention is novel 2′,5′-dideoxy-5-fluorouridine derivatives of general formula 1.

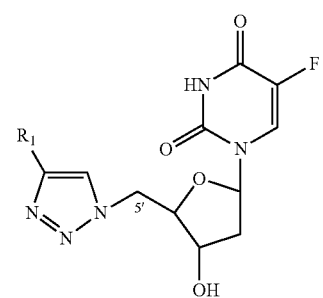

(1)

wherein $R_1$ denotes *cinchona* alkaloid fragment with defined absolute configuration at C-8 and C-9 atoms.

In a second aspect, the subject matter of the invention is a process for the manufacture of 2′,5′-dideoxy-5-fluorouridine derivatives of general formula 1.

In a third aspect, the subject matter of the invention is an application of 2′,5′-dideoxy-5-fluorouridine derivatives of general formula 1 in the anticancer treatment of breast cancer, cervical cancer, lung cancer and nasopharynx cancer.

12 Claims, No Drawings

(56) References Cited

OTHER PUBLICATIONS

Wei et al., "Design, Synthesis, and In Vitro and In Vivo Biological Studies of a 3'-Deoxythymidine Conjugate that Potentially Kills Cancer Cells Selectively", PLOS One, 2012, 7, 12, e52199, 1-8.
Lin et al., "A Novel Synthesis and Biological Activity of Several 5-Halo-5'-amino Analogues of Deoxyribopyrimidine Nucleosides", *J Med. Chem.*, 1978, 21, 1, 106-109.
Jarrahpour et al., "Petra, Osiris and Molinspiration (POM) together as a successful support in drug design: antibacterial activity and biopharmaceutical characterization of some azo Schiff bases", *Med. Chem. Res.*, 2012, 21, 1984-1990.
U.S. Appl. No. 14/413,560, filed Jan. 8, 2015 in the name of Celewicz et al.
International Search Report issued on May 13, 2014 in International Application No. PCT/PL2014/050009.
Written Opinion of the International Searching Authority issued on May 13, 2014 in International Application No. PCT/PL2014/050009.
International Search Report issued on May 23, 2014 in International Application No. PCT/PL2014/050010.
Written Opinion of the International Searching Authority issued on May 23, 2014 in International Application No. PCT/PL2014/050010.

\* cited by examiner

2', 5'-DIDEOXY-5-FLUOROURIDINE DERIVATIVES HAVING CYTOTOXIC ACTIVITY, A PROCESS FOR THE MANUFACTURE THEREOF AND APPLICATION THEREOF

The subject matter of the invention is novel 2',5'-dideoxy-5-fluorouridine derivatives and a process for the manufacture thereof and also their application as cytotoxic agents.

Cancer diseases are one of the principal health disorders reported in humans, having the highest mortality rates and increasing numbers of new cases, related first of all to the increased life length and to lifestyle. The treatment of cancer diseases is difficult, expensive and in many cases not efficacious. Therefore, there is an urgent need for novel substances with cytostatic activity. They may be sourced from natural products and their derivatives as well as constitute synthetic compounds.

Derivatives or analogues of purine or pyrimidine bases and modified nucleosides are a very important group of synthetic cytostatic agents. These include compounds, such as 5-fluorouracil (5FU) and its prodrugs, e.g. 5-fluoro-2'-deoxyuridine (floxuridine, 5FdU). Both 5-fluorouracil and 5-fluoro-2'-deoxyuridine have similar cytostatic activity, being used in the treatment of cancer, such as breast cancer, gastric cancer, colorectal cancer, ovarian cancer and the like, either in monotherapy or combined with each other or with other agents. 5-fluoro-2'-deoxyuridine is also used in the treatment of hepatic cancer owing to better hepatic metabolism compared to 5-fluorouracil. Difficulties with using 5-fluorouracil and 5-fluoro-2'-deoxyuridine are related to the development of cancer cell resistance to those agents due to their long-term intake. Furthermore, a significant limitation is relatively high toxicity of 5-fluorouracil responsible for neurotoxic and cardiotoxic effects. Moreover, as the agents are not selective with respect to cancerous and normal cells, their application in therapy is considerably limited. Another major issue is the low bioavailability of 5-fluoro-2'-deoxyuridine related to its highly negative partition coefficient (log P=−1.72); therefore, the agent is excessively polar to cross lipid cell membranes, being administered by intravenous infusion.

Attempts have been made to solve those problems through modifications of 5-fluoro-2'-deoxyuridine, such as by changing the substituent at position 5'. Amino and azido groups were reported to reduce cytostatic activity with respect to the activity of 5-fluoro-2'-deoxyuridine. High cytostatic activity of 5'-azido-2',5'-dideoxy-5-fluorouridine (5AddFU) expressing as 100% of cell growth inhibition, was reported in the available in vitro studies at concentrations as high as 400 µM. Unfortunately, the compounds did not have any selectivity between mouse tumour cells (S-180 line) and non-cancerous VERO cells (Lin, T.-S., Prusoff, W. H. *J. Med. Chem.*, 1978, 21, 106-109). Thorough cytotoxicity studies of 5'-azido-2',5'-dideoxy-5-fluorouridine (5AddFU) using four cancer cell lines (discussed in detail below) showed, however, that the compound had higher activity than that of 5-fluoro-2'-deoxyuridine and 5-fluorouracil, all the three compounds being, though, within a range for medium-activity compounds.

The objective of the present invention was to develop novel cytotoxic compounds, being 5-fluoro-2'-deoxyuridine derivatives with activity higher than or comparable to the known and already used 5-fluoro-2'-deoxyuridine and 5'-azido-2',5'-dideoxy-5-fluorouridine.

The subject matter of the invention is 2',5'-dideoxy-5-fluorouridine derivatives of general formula 1.

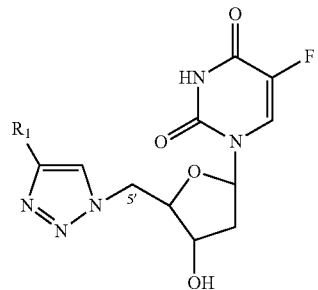

(1)

wherein:

$R_1$ denotes fragment of a *cinchona* alkaloid of natural origin obtained from bark or other parts of *Cinchona* species plants or synthetic of general formula 2 or 3 and with defined absolute configuration at C-8 and C-9 atoms which includes all four possible diastereomeric forms, that is (8R,9S) or (8S,9R) or (8R,9R) or (8S,9S). Common numbering used in *cinchona* alkaloid chemistry was used to define absolute configuration.

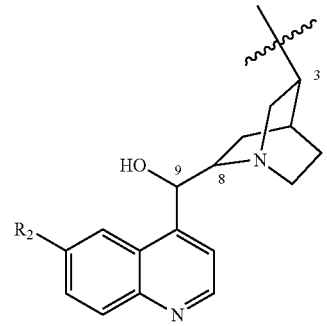

(2)

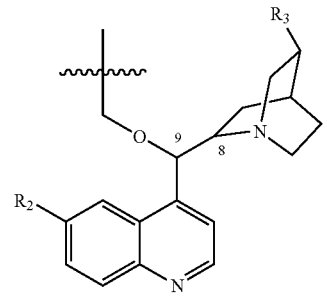

(3)

wherein:

$R_2$ denotes hydroxy group, H or an alkoxy group containing between 1 and 12 carbon atoms in a straight or branched chain or a cycloalkyl substituent containing between 3 and 10 C atoms, preferably methoxy group.

$R_3$ denotes vinyl, ethyl or acetylene group.

In the second aspect the subject matter of the invention is salts of 2',5'-dideoxy-5-fluorouridine derivatives:

monosalts of general formula 4 and 5 disalts of general formula 6, wherein a double protonated alkaloid fragment is the dication.

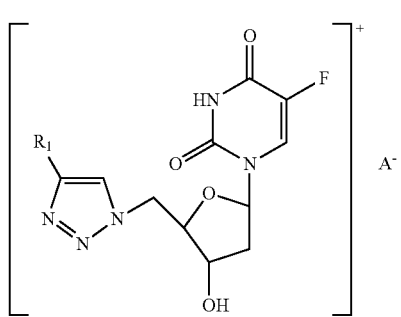

(4)

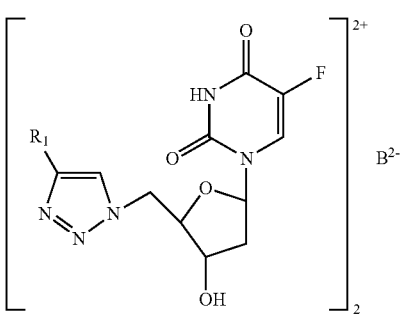

(5)

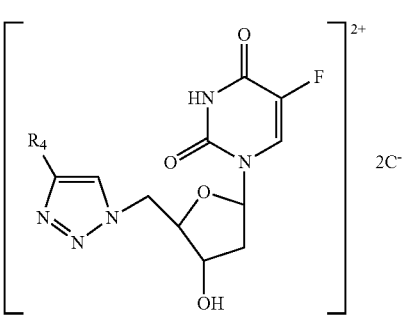

(6)

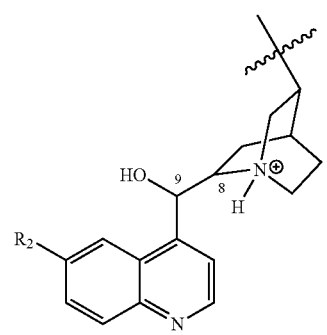

(7)

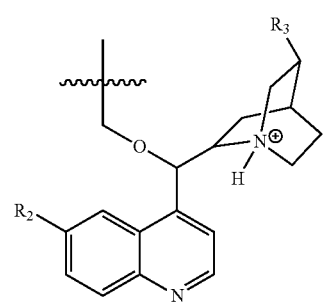

(8)

wherein:

$R_2$ denotes hydroxy group, H or an alkoxy group containing between 1 and 12 C atoms in a straight or branched chain or a cycloalkyl substituent containing between 3 and 10 C atoms, preferably methoxy group.

$R_3$ denotes vinyl, ethyl or acetylene group.

$R_4$ denotes double protonated dication of a fragment of a Cinchona alkaloid of natural origin obtained from bark or other parts of Cinchona species plants or synthetic of general formula 9 or 10 and with defined absolute configuration at C-8 and C-9 atoms which includes all four possible diastereomeric forms, that is (8R,9S) or (8S,9R) or (8R,9R) or (8S,9S). Common numbering used in cinchona alkaloid chemistry was used to define absolute configuration. Dication $R_4$ forms in the reaction of a strong monoprotic acid in a quantity higher than one equivalent with the starting compound of general formula 1.

wherein:

$A^-$ denotes Cl$^-$, Br$^-$, I$^-$, NO$_3^-$, HCOO$^-$, CH$_3$COO$^-$, CH$_3$SO$_3^-$, CH$_3$C$_6$H$_4$SO$_3^-$, CH$_3$CH(OH)COO$^-$, HOOC(CHOH)$_2$COO$^-$, HOOC(CH$_2$)$_2$COO$^-$, cis-C$_4$H$_3$O$_4^-$, trans-C$_4$H$_3$O$_4^-$, HOCH$_2$(CHOH)$_4$COO$^-$, C$_6$H$_8$O$_6^-$, C$_6$H$_7$O$_7^-$ $B^{2-}$ denotes SO$_4^{2-}$, HPO$_4^{2-}$, $^-$OOC(CH$_2$)$_2$COO$^-$, $^-$OOC(CHOH)$_2$COO$^-$, cis-C$_4$H$_2$O$_4^{2-}$, trans-C$_4$H$_2$O$_4^{2-}$ $C^-$ denotes Cl$^-$, Br$^-$, I$^-$, NO$_3^-$, CH$_3$SO$_3^-$.

$R_1$ denotes monocation of the fragment of Cinchona alkaloid of natural origin obtained from bark or other parts of Cinchona species plants or synthetic of general formula 7 or 8 and with defined absolute configuration at C-8 and C-9 atoms which includes all four possible diastereomeric forms, that is (8R,9S) or (8S,9R) or (8R,9R) or (8S,9S). Common numbering used in cinchona alkaloid chemistry was used to define absolute configuration.

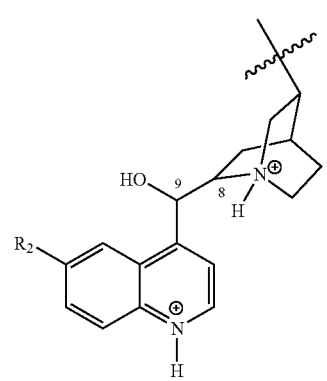

(9)

-continued

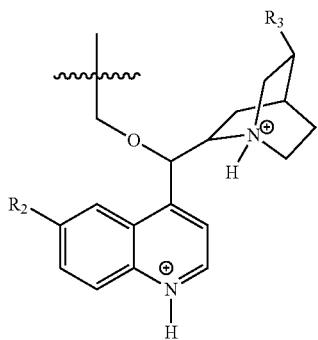

(10)

wherein:

R$_2$ and R$_3$ are as defined above.

In a third aspect, the subject matter of the invention is a process for the manufacture of 2',5'-dideoxy-5-fluorouridine derivatives of general formula 1, wherein R$_1$, R$_2$ and R$_3$ are as defined hereinabove, involving copper(I)-catalysed 1,3-dipolar Huisgen cycloaddition between 5'-azido-2',5'-dideoxy-5-fluorouridine (5AddFU) of general formula 11

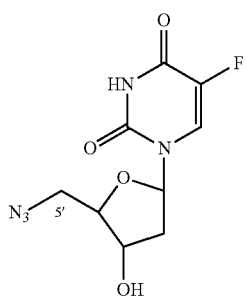

(11)

and an appropriate alkyne derivative of a *cinchona* alkaloid of general formula 12 or 13,

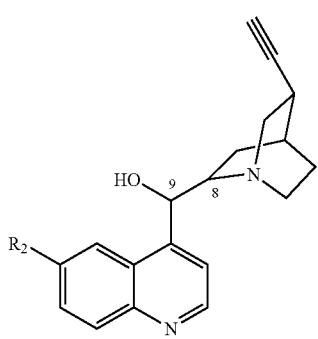

(12)

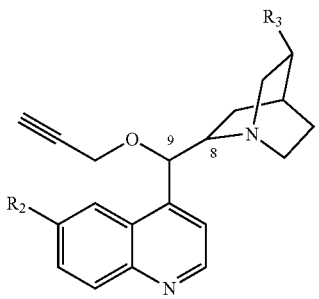

(13)

wherein R$_2$ and R$_3$ are as defined hereinabove.

Table 1 shows examples of the compounds of the invention and appropriate alkyne derivatives of *cinchona* alkaloids 12 or 13, used in the synthesis of respective compounds.

The reaction proceeds at any proportion between the azide and the alkaloid alkyne derivative; however, considering the yield of synthesis, an equimolar ratio between the reagents is preferable. The reaction is carried out in aqueous-organic mixtures with a water content of from 1% to 99% and a water-miscible organic solvent selected from the group of lower aliphatic alcohols, aliphatic ketones, cyclic ethers or aliphatic nitriles. Methanol, ethanol, tert-butanol, dioxane, acetone or acetonitrile are preferably used, and the reaction is carried out most preferably in a dioxane-water or methanol-water mixture at a volume ratio of 1:1. The reaction proceeds in a wide range of temperatures between 0° C. and 90° C.; due to practical reasons, however, the reaction is preferably carried out at room temperature.

The reaction is catalysed by Cu(I) ions which may be added directly as copper(I) salts, most preferably in the form of copper(I) iodide, or generated directly in the reaction vessel. More preferably, the Cu(I) ions which catalyse the reaction are formed in situ in the reaction mixture by reducing Cu(II) ions of any soluble copper (II) salt, preferably copper(II) sulphate pentahydrate, and an inorganic reducing agent, in particular water-soluble sulphites, metallic copper or an organic reducing agent, in particular hydroxylamine, hydroquinone or, most preferably, sodium ascorbate.

In a direct synthesis using a copper(I) salt as the catalyst, it is used in a quantity of between 0.01 and 1.0 equivalents of Cu(I) ions with respect to 5'-azido-2',5'-dideoxy-5-fluorouridine. In the second variant where the required copper(I) ions are formed in situ, a copper(II) salt is used in a quantity of between 0.01 and 1.0 equivalent of Cu(II) ions with respect to 5'-azido-2',5'-dideoxy-5-fluorouridine, preferably 0.75 equivalent of copper(II) sulphate and between 0.01 and 1.0 equivalent of the reducing agent, preferably an organic reducing agent, with respect to 5'-azido-2',5'-dideoxy-5-fluorouridine, most preferably sodium ascorbate in a quantity of 0.75 equivalent. In the variant of synthesis with the use of Cu(I) ions formed in situ, it is most preferable to use the same or larger amount of sodium ascorbate with respect to the copper(II) salt due to the instability of copper(I) ions and their oxidation by oxygen to catalytically inactive copper(II) salts.

The resulting product is isolated from the reaction mixture by being removed from the solvent mixture and purified using column chromatography on silica gel, preferably using chloroform followed by a chloroform-methanol mixture containing between 1% and 50% by volume of methanol, preferably 10% as the mobile phase.

Monosalts of 2',5'-dideoxy-5-fluorouridine derivatives of general formula 4 are obtained in a reaction between a compound of general formula 1 with no more than an equimolar quantity of a respective inorganic or organic acid.

Monosalts of general formula 5 are obtained in a reaction between a compound of general formula 1 with no more than a half equivalent of a respective diprotic inorganic or organic acid.

Disalts of general formula 6 are obtained in a reaction between one equivalent of a compound of general formula 1 with more than one equivalent of a respective monoprotic acid; preferably, two equivalents of the acid are used. When one to two equivalents of the acid are used, a mixture of mono- and disalts is obtained.

Preparations of the salts of general formulae 4, 5 or 6 are carried out in polar solvents, such as: aliphatic alcohols containing from 1 to 3 carbon atoms in the chain, DMF, DMSO, acetonitrile or mixtures thereof with water in a quantity of from 1 to 90% (v/v), preferably in a quantity of 50% water, still most preferably in methanol or ethanol.

The resulting salts are isolated by removing the solvent in a vacuum evaporator or by slow crystallisation.

| No. | Formula | Abbreviated name | Name | Absolute configuration at C8 and C9 atoms in the product | Alkaloid substrate for synthesis |
|---|---|---|---|---|---|
| 1. | (structure) | QN5AFU | 5-Fluoro-1-[4-hydroxy-5-(4-{6-[hydroxy-(6-methoxy-quinolin-4-yl)-methyl]-1-aza-bicyclo[2.2.2]oct-3-yl}-[1,2,3]triazol-1-ylmethyl)-tetrahydrofuran-2-yl]-1H-pyrimidine-2,4-dione | (8S,9R) | (8S,9R)-10,11-didehydroquinine |
| 2. | (structure) | QD5AFU | 5-Fluoro-1-[4-hydroxy-5-(4-{6-[hydroxy-(6-methoxy-quinolin-4-yl)-methyl]-1-aza-bicyclo[2.2.2]oct-3-yl}-[1,2,3]triazol-1-ylmethyl)-tetrahydrofuran-2-yl]-1H-pyrimidine-2,4-dione | (8R,9S) | (8R,9S)-10,11-didehydro-quinidine |

-continued

| No. | Formula | Abbreviated name | Name | Absolute configuration at C8 and C9 atoms in the product | Alkaloid substrate for synthesis |
| --- | --- | --- | --- | --- | --- |
| 3. | | CD5AFU | 5-Fluoro-1-(4-hydroxy-5-{4-[6-(hydroxy-quinolin-4-yl-methyl)-1-aza-bicyclo[2.2.2]oct-3-yl]-[1,2,3]triazol-1-ylmethyl}-tetrahydrofuran-2-yl)-1H-pyrimidine-2,4-dione | (8S,9R) | (8S,9R)-10,11-didehydro-cinchonidine |
| 4. | | CN5AFU | 5-Fluoro-1-(4-hydroxy-5-{4-[6-(hydroxy-quinolin-4-yl-methyl)-1-aza-bicyclo[2.2.2]oct-3-yl]-[1,2,3]triazol-1-ylmethyl}-tetrahydrofuran-2-yl)-1H-pyrimidine-2,4-dione | (8R,9S) | (8R,9S)-10,11-didehydro-cinchonine |
| 5. | | PQN5AFU | 5-Fluoro-1-(4-hydroxy-5-{4-[(6-methoxy-quinolin-4-yl)-(5-vinyl-1-aza-bicyclo[2.2.2]oct-2-yl)-methoxymethyl]-[1,2,3]triazol-1-ylmethyl}-tetrahydrofuran-2-yl)-1H-pyrimidine-2,4-dione | (8S,9R) | (8S,9R)-9-O-propargylquinine |

-continued

| No. | Formula | Abbreviated name | Name | Absolute configuration at C8 and C9 atoms in the product | Alkaloid substrate for synthesis |
|---|---|---|---|---|---|
| 6. | [structure] | PQD5AFU | 5-Fluoro-1-(4-hydroxy-5-{4-[(6-methoxy-quinolin-4-yl)-(5-vinyl-1-aza-bicyclo[2.2.2]oct-2-yl)-methoxymethyl]-[1,2,3]triazol-1-ylmethyl}-tetrahydrofuran-2-yl)-1H-pyrimidine-2,4-dione | (8R,9S) | (8R,9S)-9-O-propargyl-quinidine |
| 7. | [structure] | PCD5AFU | 5-Fluoro-1-(4-hydroxy-5-{4-[quinolin-4-yl-(5-vinyl-1-aza-bicyclo[2.2.2]oct-2-yl)-methoxymethyl]-[1,2,3]triazol-1-ylmethyl}-tetrahydrofuran-2-yl)-1H-pyrimidine-2,4-dione | (8S,9R) | (8S,9R)-9-O-propargyl-cinchonidine |
| 8. | [structure] | PCN5AFU | 5-Fluoro-1-(4-hydroxy-5-{4-[quinolin-4-yl-(5-vinyl-1-aza-bicyclo[2.2.2]oct-2-yl)-methoxymethyl]-[1,2,3]triazol-1-ylmethyl}-tetrahydrofuran-2-yl)-1H-pyrimidine-2,4-dione | (8R,9S) | (8R,9S)-9-O-propargyl-cinchonine |

In a fourth aspect, the subject matter of the invention is an application of 2',5'-dideoxy-5-fluorouridine derivatives of general formula 1 and pharmaceutically acceptable salts thereof of the invention in the anticancer treatment of breast cancer, cervical cancer, lung cancer and nasopharynx cancer. In vitro studies on cancer cell lines of breast cancer, cervical cancer, lung cancer and nasopharynx cancer confirmed cytotoxic action (Table 2). In most cases, the activity of compounds of general formula 1 exceeds that of 2'-deoxy-5-fluorouridine, 5-fluorouracil and 5'-azido-2',5'-dideoxy-5-fluorouridine when tested in the same conditions.

Cytotoxic activity tests were performed using the following cancer cell lines: MCF-7 (breast cancer), HeLa (cervical cancer) A549 (lung cancer) and KB (nasopharynx cancer) obtained from ECACC (European Collection of Cell Cultures).

Cytotoxicity tests were carried out using a standard procedure with sulphorhodamine B. They involved incubation of the cancer cell lines in the logarithmic growth phase for 72 hours with the compound tested and, subsequently, spectrophotometric determination of the degree of cell growth inhibition using adsorption of a dye (sulphorhodamine B) which binds cellular proteins. The determination was carried out according to a procedure reported in: Vichai, V., Kirtikara, K. *Nature Protocols,* 2006, 1, 1112.

Determination of Cytotoxicity

Preparation of Cells for the Experiment:

Cells of the cell line tested in the logarithmic growth phase were seeded onto 24-well plates in a quantity of 20,000 cells/2 mL of the growth medium per well and, subsequently, incubated in an incubator at 37° C., in the 5% $CO_2$ atmosphere for 24 hours.

Preparation of Test Compound Solutions:

Solutions of the test compounds were prepared in DMSO in the following concentration range: 0.05; 0.1; 0.5; 1; 5; 10; 50; 100; 500 µM.

The cells of the lines tested were treated with the solutions of the test compounds in a laminar-flow chamber which ensured sterile working conditions according to the following procedure: the first three wells were used as a control: they contained 20 µL of DMSO only; successive solutions of the test compound were added to subsequent wells (20 µL), starting with the lowest concentration (three wells for each concentration level). Subsequently, the plates were placed in an incubator for 72 hours.

After the end of incubation, the adhered cells were fixed by adding 500 µL of cold (4° C.) 50% trichloroacetic acid (TCA) and incubated at 4° C. for 1 hour. Subsequently, each well was rinsed with sterile water and dried. The operation was repeated five times. The fixed cells were stained for 30 minutes by adding 500 µL of 0.4% of a dye solution (sulphorhodamine B) dissolved in 1% acetic acid. Any unbound dye was removed by decanting it from the plate, and the cells were washed 4 times with 1% acetic acid. Subsequently, the plates were dried in air for approx. 5 minutes. Any unbound dye was dissolved by adding 1500 µL of 10 mM Tris-base buffer (trishydroxymethylaminomethane) to each well and shaken using an orbital shaker for 5 minutes. Subsequently, 200 µL of solution from each well was transferred to each of two wells on a new 96-well plate and absorption of the solutions was determined spectrophotometrically at a wavelength of 490-530 nm using a plate reader. Percentage inhibition of cell growth by the test compound was calculated assuming the absorption of the control solution as 100%.

Cytotoxicity tests for the other compounds and cell lines were performed following an identical procedure.

Depending on the type of the cell line, the following growth media were used:

the MCF-7 line was grown in Dulbecco's Modified Eagle's Medium (DME) from Sigma (cat. no. D5796)

the HeLa, A549 and KB lines were grown in RPMI-1640 Medium from Sigma (cat. no. R8758).

$IC_{50}$ values, being concentration of a compound needed to obtain 50% inhibition of cell growth, were determined for all the derivatives tested. Derivatives for which $IC_{50}$<4 µg/mL are generally assumed as active (abbreviated as A), derivatives with values in an $IC_{50}$ range of 4-30 µg/mL are considered medium active (abbreviated as MA), while those for which $IC_{50}$>30 µg/mL are considered non-active (abbreviated as NA).

To enable comparison, identical tests were performed using known cytotoxic agents: 5-fluoro-2'-deoxyuridine, 5-fluorouracil and 5'-azido-2',5'-dideoxy-5-fluorouridine.

The results of cytotoxic activity tests for the compounds of general formula 1 are shown in Table 2. The values are average results of three independent determinations.

TABLE 2

| | Cytotoxic activity, $IC_{50}$ | | | | | | | | |
|---|---|---|---|---|---|---|---|---|---|
| | MCF-7 line (breast cancer) | | HeLa (cervical cancer) | | A549 (lung cancer) | | KB (nasopharynx cancer) | | Calculated partition |
| Compound | [µg/mL] | [µmol] | [µg/mL] | [µmol] | [µg/mL] | [µmol] | [µg/mL] | [µmol] | coefficient, logP |
| QN5AFU | 12.0 (MA) | 20.22 | 12.0 (MA) | 20.22 | 16.0 (MA) | 26.95 | 12.6 (MA) | 21.23 | 0.40 |
| QD5AFU | 6.1 (MA) | 10.28 | 7.3 (MA) | 12.30 | 8.0 (MA) | 13.48 | 8.9 (MA) | 15.00 | 0.40 |
| CD5AFU | 11.4 (MA) | 20.23 | 13.0 (MA) | 23.07 | 15.2 (MA) | 26.97 | 15.0 (MA) | 26.62 | 0.36 |
| CN5AFU | 2.8 (A) | 4.97 | 3.1 (A) | 5.5 | 3.1 (A) | 5.5 | 2.9 (A) | 5.15 | 0.36 |
| PQN5AFU | 27.0 (MA) | 42.61 | 29.0 (MA) | 45.77 | 29.4 (MA) | 46.40 | 31.0 | 48.92 | 2.17 |
| PQD5AFU | 16.0 (MA) | 25.25 | 19.1 (MA) | 30.14 | 19.7 (MA) | 31.09 | 19.5 (MA) | 30.77 | 2.17 |
| PCD5AFU | 11.8 (MA) | 19.55 | 18.8 (MA) | 29.82 | 17.8 (MA) | 29.49 | 17.5 (MA) | 28.99 | 2.13 |
| PCN5AFU | 2.4 (A) | 3.98 | 2.7 (A) | 4.47 | 2.7 (A) | 4.47 | 2.4 (A) | 3.98 | 2.13 |
| PCN5AFU dihydrochloride | 1.7 (A) | 2.51 | 2.7 (A) | 3.99 | 3.0 (A) | 4.43 | 2.0 (A) | 2.96 | 0.16 |
| 5-fluoro-2'-deoxyuridine | 2.81 (A) | 11.4 | 3.20 (A) | 13.0 | 3.30 (A) | 13.4 | 3.37 (A) | 13.7 | −1.72 |
| 5-fluorouracil | 2.37 (A) | 18.2 | 2.73 (A) | 21.0 | 2.78 (A) | 21.4 | 2.86 (A) | 22.0 | −0.59 |
| 5'-azido-2',5'-dideoxy-5-fluorouridine | 7.4 (MA) | 27.29 | 7.8 (MA) | 28.76 | 7.0 (MA) | 25.81 | 7.0 (MA) | 25.81 | −0.38 |

The cytotoxicity of all the compounds being the subject matter of the application was tested as high for 5-fluoro-1-(4-hydroxy-5-{4-[6-(hydroxy-quinolin-4-yl-methyl)-1-aza-bicyclo[2.2.2]oct-3-yl]-[1,2,3]triazol-1-ylmethyl}-tetrahydro-furan-2-yl)-1H-pyrimidine-2,4-dione with (8R,9S) configuration of the alkaloid moiety (CN5AFU) and 5-fluoro-1-(4-hydroxy-5-{4-[quinolin-4-yl-(5-vinyl-1-aza-bicyclo[2.2.2]oct-2-yl)-methoxymethyl]-[1,2,3]triazol-1-yl-methyl}-tetrahydro-furan-2-yl)-1H-pyrimidine-2,4-dione with (8R,9S) configuration of the alkaloid moiety (PCN5AFU). Medium cytotoxic activity was confirmed for the reference drugs: 2'-deoxy-5-fluorouridine (5FdU), 5-fluorouracil (5FU) and a synthetic nucleotide, 5'-azido-2', 5'-dideoxy-5-fluorouridine (5AddFU).

In a further aspect, the subject matter of the application is in particular the application of 5-fluoro-1-(4-hydroxy-5-{4-[6-(hydroxy-quinolin-4-yl-methyl)-1-aza-bicyclo[2.2.2]oct- 3-yl]-[1,2,3]triazol-1-ylmethyl}-tetrahydro-furan-2-yl)-1H-pyrimidine-2,4-dione with (8R,9S) configuration of the alkaloid moiety (CN5AFU) or 5-fluoro-1-(4-hydroxy-5-{4-[quinolin-4-yl-(5-vinyl-1-aza-bicyclo[2.2.2]oct-2-yl)-methoxymethyl]-[1,2,3]triazol-1-ylmethyl}-tetrahydro-furan-2-yl)-1H-pyrimidine-2,4-dione with (8R,9S) configuration of the alkaloid moiety (PCN5AFU) and their pharmaceutically acceptable salts for the manufacture of drugs used in the chemotherapy of breast cancer.

It was confirmed in the tests performed that CN5AFU ($IC_{50}$=2.8 µg/mL) and PCN5AFU ($IC_{50}$=2.4 µg/mL) had the highest activity against breast cancer cells, having 1.4-fold higher activity than 5FU, 1.6-fold higher activity than 5FdU and 3-fold higher activity than 5AddFU, respectively.

In a further aspect, the subject matter of the application is in particular the application of 5-fluoro-1-(4-hydroxy-5-{4-[6-(hydroxy-quinolin-4-yl-methyl)-1-aza-bicyclo[2.2.2]oct-3-yl]-[1,2,3]triazol-1-ylmethyl}-tetrahydro-furan-2-yl)-1H-pyrimidine-2,4-dione with (8R,9S) configuration of the alkaloid moiety (CN5AFU) or 5-fluoro-1-(4-hydroxy-5-{4-[quinolin-4-yl-(5-vinyl-1-aza-bicyclo[2.2.2]oct-2-yl)-methoxymethyl]-[1,2,3]triazol-1-ylmethyl}-tetrahydro-furan-2-yl)-1H-pyrimidine-2,4-dione with (8R,9S) configuration of the alkaloid moiety (PCN5AFU) and their pharmaceutically acceptable salts for the manufacture of drugs used in the chemotherapy of cervical cancer.

It was confirmed in the tests performed that PCN5AFU ($IC_{50}$=2.7 µg/mL) and CN5AFU ($IC_{50}$=3.1 µg/mL) had the highest activity against cervical cancer cells, having comparable activity to 5FU, more than 1.2-fold higher activity than 5FdU and more than 2-fold higher activity than 5AddFU.

In a further aspect, the subject matter of the application is in particular the application of 5-fluoro-1-(4-hydroxy-5-{4-[6-(hydroxy-quinolin-4-yl-methyl)-1-aza-bicyclo[2.2.2]oct-3-yl]-[(1,2,3]triazol-1-ylmethyl}-tetrahydrofuran-2-yl)-1H-pyrimidine-2,4-dione with (8R,9S) configuration of the alkaloid moiety (CN5AFU) or 5-fluoro-1-(4-hydroxy-5-{4-[quinolin-4-yl-(5-vinyl-1-aza-bicyclo[2.2.2]oct-2-yl)-methoxymethyl]-[1,2,3]triazol-1-ylmethyl}-tetrahydro-furan-2-yl)-1H-pyrimidine-2,4-dione with (8R,9S) configuration of the alkaloid moiety (PCN5AFU) and their pharmaceutically acceptable salts for the manufacture of drugs used in the chemotherapy of lung cancer.

It was confirmed in the tests performed that PCN5AFU ($IC_{50}$=2.7 µg/mL) and CN5AFU ($IC_{50}$=3.1 µg/mL) had the highest activity against lung cancer cells, having more than 1.03-fold higher activity than 5FU, more than 1.2-fold higher activity than 5FdU and more than 2-fold higher activity than 5AddFU.

In a further aspect, the subject matter of the application is in particular the application of 5-fluoro-1-(4-hydroxy-5-{4-[6-(hydroxy-quinolin-4-yl-methyl)-1-aza-bicyclo[2.2.2]oct-3-yl]-[1,2,3]triazol-1-ylmethyl}-tetrahydro-furan-2-yl)-1H-pyrimidine-2,4-dione with (8R,9S) configuration of the alkaloid moiety (CN5AFU) or 5-fluoro-1-(4-hydroxy-5-{4-[quinolin-4-yl-(5-vinyl-1-aza-bicyclo[2.2.2]oct-2-yl)-methoxymethyl]-[1,2,3]triazol-1-ylmethyl}-tetrahydro-furan-2-yl)-1H-pyrimidine-2,4-dione with (8R,9S) configuration of the alkaloid moiety (PCN5AFU) and their pharmaceutically acceptable salts thereof for the manufacture of drugs used in the chemotherapy of nasopharynx cancer.

It was confirmed in the tests performed that PCN5AFU ($IC_{50}$=2.4 µg/mL) and CN5AFU ($IC_{50}$=2.9 µg/mL) had the highest activity against nasopharynx cancer cells, having more than 1.4-fold higher activity than 5FU, more than 1.7-fold higher activity than 5FdU and more than 2-fold higher activity than 5AddFU.

The absolute configuration at C-8 and C-9 atoms is important for cytotoxic activity in the group of compounds of general formula 1. Cinchonine derivatives (CN5AFU and PCN5AFU) with absolute configuration (8R,9S) in the alkaloid moiety had the highest activity.

The other important indicator which determines whether a drug is able to cross lipid biological membranes and thus enables its transport and distribution is the partition coefficient, log P. When the coefficient has a negative value, a drug is excessively polar, water-soluble and unable to penetrate across biological membranes; this leads to low bioavailability and limited transport. Desired values of the log P partition coefficient for most drugs are within a range of between 2 and 4; for example, average log P values for large collections of drugs and natural products are within a range of 2.2-2.4 (K. Grabowski, G. Schneider, Curr. Chem. Biol., 2007, 1, 115-127; G. Vistoli, A. Pedretti, B. Testa, Drug Discov. Today 2008, 13, 285).

5-Fluoro-2'-deoxyuridine and 5'-azido-5',3'-dideoxy-5-fluorouridine have undesirable (negative) log P values of −1.72 and −0.38, respectively.

Log P partition coefficient values for the compounds of general formula 1 (Table 2) were calculated with commonly used computational algorithms using molinspiration software (Molinspiration Cheminformatics, available in 2013 at the following website: http://www.molinspiration.com/services/) and Jarrahpour, A. et al. Med. Chem. Res., 2012, 21, 1984).

The resulting data (Table 2) confirmed that the presence of a large alkaloid moiety in the molecules of the compounds of general formula 1 results in a much increased value of the partition coefficient (log P) compared to the reference compounds (5-fluorouracil, 5-fluoro-2'-deoxyuridine and 5'-azido-2',5'-dideoxy-5-fluorouridine). In consequence, easier penetration of compounds of general formula 1 across biological membranes improves transport and distribution.

The subject matter of the invention is explained using certain embodiments which illustrating but not limiting the invention.

In the examples, alkyne derivatives of cinchona alkaloids: quinine, quinidine, cinchonine and cinchonidine isolated from cinchona bark, were prepared following procedures as reported in the literature. For the derivatives used in the synthesis of compounds QN5AFU, QD5AFU, CD5AFU and CN5AFU, according to K. M. Kacprzak, W. Lindner, N. M. Maier, Chirality, 2008, 20, 441; for the synthesis of compounds PQN5AFU, PQD5AFU, PCD5AFU and PCN5AFU, according to a procedure disclosed in Patent EP1477488 (2004).

Solvents and other chemical reagents were obtained from Aldrich, Merck and POCh and used as received. Column chromatography was performed with silica gel 60H used as the stationary phase (0.045-0.075 mm/200-300 mesh) from Merck.

$^1$H NMR, $^{13}$C NMR and $^{19}$F NMR spectra of the compounds were recorded using Varian-Gemini (300 MHz) and Bruker Avance (600 MHz) spectrometers with the following internal standards: tetramethylsilane (TMS) when recording $^1$H NMR and $^{13}$C NMR spectra and trichlorofluoromethane ($CFCl_3$) for $^{19}$F NMR spectra. Mass spectra in ESI technique were recorded using Varian LC-MS instrument.

EXAMPLE 1

Synthesis of 5'-Azido-2',5'-dideoxy-5-fluorouridine

A. 5'-O-Tosyl-2',5'-dideoxy-5-fluorouridine

In a round-bottomed flask fitted with a magnetic stirrer, 5-fluoro-2'-deoxyuridine (1.02 g, 4.15 mmol) and dry pyridine (41.50 mL) were placed. The flask was cooled to 0° C. on an ice bath. Subsequently, p-toluenesulphonic acid chloride (1.04 g; 5.4 mmol) was added to the solution stirred vigorously. The stirring was continued until the tosyl chloride dissolved. The reaction flask was left to stand in a refrigerator at 0-5° C. for 48 hours. When the reaction was completed, most pyridine was evaporated under reduced pressure, and any residual pyridine was removed by evaporating the crude product three times with toluene added (20 mL) under reduced pressure. The resulting crude product was purified on a chromatographic column with silica gel using a chloroform-methanol mixture (1 to 10% v/v) as the eluent. 5'-O-Tosyl-2',5'-dideoxy-5-fluorouridine was obtained as white powder with a yield of approx. 65%.

B. 5'-Azido-2',5'-dideoxy-5-fluorouridine (5AddFU)

In a two-necked round-bottomed flask fitted with a reflux condenser with a drying tube with anhydrous $CaCl_2$, a thermometer and a magnetic stirrer 5'-O-(4-toluenesulphonyl)-2',5'-dideoxy-5-fluorouridine (1.083 g, 2.70 mmol), prepared in step A and dried in a vacuum desiccator, and dry DMF (27 mL) were placed. The solution was stirred until the substrate dissolved; subsequently, lithium chloride (0.21 g, 4.86 mmol) and sodium azide (0.297 g; 4.86 mmol) were added. The stirred solution was heated at 100° C. for 3 hours. Subsequently, the solvent was evaporated using a vacuum evaporator under reduced pressure. The crude product was purified on a chromatographic column with silica gel using a chloroform-methanol mixture (gradient: 1 to 10% v/v) as the eluent. Pure 5'-azido-2',5'-dideoxy-5-fluorouridine (5AddFU) was obtained as white powder with a yield of approx. 70%.

EXAMPLE 2

Synthesis of Compound QN5AFU

In a round-bottomed flask, AddFU (82 mg; 0.30 mmol) obtained according to Example 1 and an equimolar amount of 10,11-didehydroquinine (97 mg; 0.302 mmol) were placed. The substrates were dissolved in 1,4-dioxane (4 mL) and stirred using a magnetic stirrer at room temperature until dissolved completely. Subsequently, sodium ascorbate (48 mg; 0.24 mmol) and distilled water (1 mL) were added. The mixture was stirred until a homogenous solution was obtained. Finally a 1M $CuSO_4$ solution (0.25 mL; 0.24 mmol) was added. The reaction mixture was vigorously stirred for 24 hours at room temperature. When the reaction was completed, the solvent was removed using a rotary evaporator, and the compound was purified on a chromatographic column with silica gel using a chloroform-methanol mixture (20:1, v/v) as the eluent. Following chromatographic purification, 5-fluoro-1-[4-hydroxy-5-(4-{6-[hydroxy-(6-methoxy-quinolin-4-yl)-methyl]-1-aza-bicyclo[2.2.2]oct-3-yl}-[1,2,3]triazol-1-ylmethyl)-tetrahydro-furan-2-yl]-1H-pyrimidine-2,4-dione with (8S,9R) configuration of the alkaloid moiety was obtained with 66% yield.

$^1$H NMR (400 MHz, DMSO-$d_6$): δ 1.44 (m, 1H), 1.60-1.69 (m, 3H), 2.03-2.67 (m, 4H), 2.99 (m, 1H), 3.08 (m, 1H), 3.15-3.90 (m, 6H), 4.01 (m, 1H), 4.21 (m, 1H), 4.58 (dd, 2H, J=5.9, 10.1), 5.52 (d, 1H, J=6.0 Hz), 6.10 (t, 1H, J=6.6 Hz), 7.40 (dd, 1H, J=2.6, 9.2 Hz), 7.51 (d, 1H, J=4.7 Hz), 7.57 (d, 1H, J=2.8 Hz), 7.83 (d, 1H, J=8.0 Hz), 7.94 (d, 1H, J=7.00 Hz), 7.98 (s, 1H), 8.68 (d, 1H, J=4.8 Hz), $^{13}$C NMR (DMSO-$d_6$): δ 23.31, 26.90, 27.89, 33.38, 37.89, 42.12, 51.81, 55.69, 58.21, 61.12, 7028, 71.01, 83.43, 84.71, 102.58, 109.47, 119.18, 121.81, 122.59, 126.74, 131.18, 136.18, 143.98, 147.15, 149.13, 149.81, 150.55, 157.12, 164.11.

$^{19}$F NMR (DMSO-$d_6$): −166.21 (d, IF, J=6.3 Hz). MS ES (m/z): 592 (M−H)$^−$, 628/630 (M+Cl)$^−$; (+) 594 (M+H)$^+$, 616 (M+Na)$^+$; 632 (M+K).

EXAMPLE 3

Synthesis of Compound QD5AFU

Using a procedure identical as in Example 2, a reaction between 82 mg (0.302 mmol) of 5AddFU and 10,11-didehydroquinidine (97 mg; 0.302 mmol) was performed. Following the chromatographic purification, 5-fluoro-1-[4-hydroxy-5-(4-{6-[hydroxy-(6-methoxy-quinolin-4-yl)-methyl]-1-aza-bicyclo[2.2.2]oct-3-yl}-[1,2,3]triazol-1-ylmethyl)-tetrahydro-furan-2-yl]-1H-pyrimidine-2,4-dione with (8R,9S) configuration of the alkaloid moiety was obtained with 65% yield.

$^1$H NMR (400 MHz, DMSO-$d_6$): δ 1.35 (m, 1H), 1.66 (m, 2H), 1.88 (m, 1H), 2.17 (s, 1H), 2.29 (m, 2H), 2.99-3.65 (m, 4H), 3.72 (m, 1H), 4.12 (s, 3H), 4.30 (m, 2H), 4.72 (m, 1H), 4.80 (m, 1H), 5.59 (m, 1H), 6.17 (t, 1H, J=7.5 Hz), 7.12 (m, 1H), 7.42 (d, 1H, J=8.1 Hz), 7.48 (s, 2H), 7.91 (m, 2H), 8.11 (s, 1H).

$^{13}$C NMR (DMSO-$d_6$): (523.30, 26.81, 28.42, 33.42, 36.14, 46.12, 48.61, 52.08, 56.41, 60.81, 70.52, 72.44, 83.91, 85.91, 103.21, 109.91, 119.11, 121.87, 122.24, 127.21, 130.94, 137.15, 145.28, 147.45, 148.99, 150.08, 150.48, 157.81, 163.94.

$^{19}$F NMR (DMSO-$d_6$): −166.07 (d, IF, J=5.4 Hz). MS ES (m/z) 592 (M−H)$^−$, 628/630 (M+Cl)$^−$; (+) 594 (M+H)$^+$, 616 (M+Na)$^+$; 632 (M+K).

EXAMPLE 4

Synthesis of Compound CD5AFU

Using a procedure identical as in Example 2, a reaction between 5AddFU (82 mg, 0.302 mmol) and 10,11-didehydrocinchonidine (88 mg; 0.302 mmol) was performed. Following the chromatographic purification, 5-fluoro-1-(4-hydroxy-5-{4-[6-(hydroxy-quinolin-4-yl-methyl)-1-aza-bicyclo[2.2.2]-oct-3-yl]-[1,2,3]triazol-1-ylmethyl}-tetrahydro-furan-2-yl)-1H-pyrimidine-2,4-dione with (8S, 9R) configuration of the alkaloid moiety was obtained with 60% yield.

$^1$H NMR (400 MHz, DMSO-$d_6$): δ 1.34 (m, 1H), 1.69 (m, 2H), 1.94 (m, 1H), 2.18 (m, 11H), 2.54 (m, 2H), 3.18-3.79 (m, 4H), 3.98 (m, 1H), 4.61 (m, 2H), 4.74 (m, 1H), 5.08 (m, 1H), 5.62 (s, 1H), 6.18 (t, 1H, J=6.5 Hz), 7.24 (s, 1H), 7.52 (m, 1H), 7.67 (m, 2H), 7.89 (m, 2H), 8.17 (m, 1H), 8.52 (m, 1H), 8.94 (m, 1H).

$^{13}$C NMR (DMSO-$d_6$): δ 19.78, 22.74, 26.74, 36.78, 38.25, 47.20, 49.58, 53.61, 57.91, 67.19, 72.14, 82.34, 85.94, 109.62, 119.87, 121.74, 122.84, 127.92, 129.58, 130.48, 136.57, 145.87, 147.15, 149.51, 150.78, 152.18, 158.17, 164.11.

$^{19}$F NMR (DMSO-d$_6$): −166.28 (d, IF, J=6.8 Hz). MS ES: m/z (−) 562 (M−H)$^−$, 598/600 (M+Cl)$^−$; 564 (M+H)$^+$, 586 (M+Na)$^+$; 602 (M+K).

EXAMPLE 5

Synthesis of Compound CN5AFU

Using a procedure identical as in Example 2, a reaction between 5AddFU (82 mg; 0.302 mmol) and 10,11-didehydrocinchonine (88.2 mg; 0.302 mmol) was performed. Following the chromatographic purification, 5-Fluoro-1-(4-hydroxy-5-{4-[6-(hydroxy-quinolin-4-yl-methyl)-1-azabicyclo[2.2.2]-oct-3-yl]-[1,2,3]triazol-1-ylmethyl}-tetrahydro-furan-2-yl)-1H-pyrimidine-2,4-dione with (8R, 9S) configuration of the alkaloid moiety was obtained with 58% yield.

$^1$H NMR (400 MHz, DMSO-d): δ 1.28 (m, 1H), 1.58 (m, 2H), 1.92 (m, 1H), 2.13 (m, 1H), 2.48 (m, 2H), 3.13-3.64 (m, 4H), 3.92 (m, 1H), 4.48 (m, 2H), 4.68 (m, 1H), 4.94 (m, 1H), 5.60 (s, 1H), 6.20 (t, 1H, J=6.8 Hz), 7.21 (s, 1H), 7.48 (m, 1H), 7.52 (m, 2H), 7.81 (m, 2H), 8.11 (m, 1H), 8.40 (m, 1H), 8.84 (m, 1H).

$^{13}$C NMR (DMSO-d$_6$): δ 19.24, 21.87, 27.48, 37.09, 38.14, 46.12, 49.27, 52.44, 58.74, 66.44, 71.08, 82.15, 85.71, 109.58, 118.94, 121.87, 122.67, 126.84, 129.41, 130.19, 136.38, 145.18, 147.79, 149.11, 150.14, 150.49, 158.15, 163.74.

$^{19}$F NMR (DMSO-d$_6$): −166.20 (d, IF, J=6.3 Hz). MS ES: m/z (−) 562 (M−H)$^−$, 598/600 (M+Cl)$^−$; 564 (M+H)$^+$, 586 (M+Na)+; 602 (M+K).

EXAMPLE 6

Synthesis of Compound PQN5AFU

Using a procedure identical as in Example 2, a reaction between 5AddFU (82 mg; 0.302 mmol) and 1-O-propargylquinine (109.4 mg; 0.302 mmol) was performed. Following chromatographic purification, 5-fluoro-1-(4-hydroxy-5-{4-[(6-methoxy-quinolin-4-yl)-(5-vinyl-1-azabicyclo[2.2.2]-oct-2-yl)-methoxymethyl]-[1,2,3]triazol-1-ylmethyl}-tetrahydro-furan-2-yl)-1H-pyrimidine-2,4-dione with (8S,9R) configuration of the alkaloid moiety was obtained with 55% yield.

$^1$H NMR (300/400 MHz, DMSO-d$_6$): δ 1.24 (m, 1H), 1.60 (s, 1H), 1.82 (s, 1H), 2.13 (m, 1H), 2.21 (m, 1H), 2.29 (s, 3H), 2.73 (s, 1H), 2.89 (s, 1H), 3.96 (m, 2H), 4.10 (dt, 1H, J=7.5, 3.9, 3.9 Hz), 4.27 (m, 1H), 4.47 (m, 1H), 4.69 (m, 1H), 4.96 (d, 1H, J=10.3 Hz), 5.03 (d, 1H, J=17.3 Hz), 5.57 (m, 1H), 5.82 (ddd, 1H, J=17.3, 10.1, 7.6 Hz), 6.14 (t, 1H, J=6.5 Hz), 7.13 (d, 2H, J=7.9 Hz), 7.45 (dd, 1H, J=9.0, 2.1 Hz), 7.55 (d, 1H, J=3.4 Hz), 7.61 (s, 1H), 7.96 (d, 1H, J=7.0 Hz), 7.99 (d, 1H, J=9.1 Hz), 8.17 (s, 1H), 8.77 (s, 1H), $^{13}$C NMR (DMSO-d$_6$): δ 8.4, 20.81, 26.87, 37.94, 51.27, 56.17, 61.77, 70.70, 84.29, 84.71, 102.19, 121.74, 124.91, 125.23, 125.53, 128.12, 131.35, 137.80, 139.01, 141.26, 146.16, 144.11, 145.47, 147.49, 149.03, 156.88, 157.14, 157.53;

$^{19}$F NMR (DMSO-d$_6$): δ −166.23; MS ES: m/z (−) 632 (M−H)$^−$, 668/671 (M+Cl)$^−$; 634 (M+H)$^+$, 656 (M+Na)$^+$.

EXAMPLE 7

Synthesis of Compound PQD5AFU

Using a procedure identical as in Example 2, a reaction between 5AddFU (82 mg; 0.302 mmol) and 9-O-propargylquinidine (109.4 mg; 0.302 mmol) was performed. Following chromatographic purification, 5-fluoro-1-(4-hydroxy-5-{4-[(6-methoxy-quinolin-4-yl)-(5-vinyl-1-azabicyclo[2.2.2]-oct-2-yl)-methoxymethyl]-[1,2,3]triazol-1-ylmethyl}-tetrahydro-furan-2-yl)-1H-pyrimidine-2,4-dione with (8R,9S) configuration of the alkaloid moiety was obtained with 60% yield.

$^1$H NMR (300/400 MHz, DMSO-d$_6$): δ 1.04 (d, 1H, J=6.1 Hz), 1.58 (s, 1H), 1.73 (s, 1H), 1.92 (s, 1H), 2.15 (dd, 1H, J=6.0, 3.6 Hz), 2.23 (d, 1H, J=5.2 Hz), 2.26 (s, 1H), 2.36 (s, 1H), 2.44 (d, 1H, J=1.6 Hz), 2.56 (m, 1H), 2.95 (m, 1H), 3.17 (s, 1H), 3.57 (s, 1H), 3.94 (m, 2H), 4.09 (dd, 1H, J=7.5, 3.6 Hz), 4.22 (d, 1H, J=3.5 Hz), 4.28 (s, 1H), 4.49 (m, 1H), 4.71 (m, 1H), 4.98 (s, 1H), 5.03 (d, 1H, J=7.1 Hz), 5.58 (s, 1H), 5.86 (ddd, 1H, J=17.3, 10.3, 7.3), 6.16 (m, 1H), 7.12 (s, 1H), 7.14 (s, 1H), 7.48 (m, 1H), 7.49 (m, 1H), 7.55 (s, 1H), 7.99 (d, 1H, J=6.0 Hz), 8.18 (m, 1H), 8.80 (s, 1H);

$^{13}$C NMR (DMSO-d$_6$): δ 20.79, 27.14, 37.94, 47.55, 48.62, 51.29, 55.80, 59.41, 61.77, 70.68, 84.32, 84.69, 102.13, 115.26, 121.63, 124.88, 125.28, 125.50, 128.09, 131.33, 137.76, 138.63, 141.63, 143.35, 144.05, 145.57, 147.49, 149.04, 156.83, 157.17, 157.41;

$^{19}$F NMR (DMSO-d$_6$): δ −166.16; MS ES: m/z (−) 632 (M−H)$^−$, 668/670 (M+Cl)$^−$; (+) 634 (M+H)$^+$.

EXAMPLE 8

Synthesis of Compound PCD5AFU

Using a procedure identical as in Example 2, a reaction between 5AddFU (82 mg; 0.302 mmol) and 9-O-propargylcinchonidine (100.4 mg; 0.302 mmol) was performed. Following chromatographic purification, 5-fluoro-1-(4-hydroxy-5-{4-[quinolin-4-yl-(5-vinyl-1-aza-bicyclo[2.2.2]oct-2-yl)-methoxymethyl]-[1,2,3]triazol-1-ylmethyl}-tetrahydro-furan-2-yl)-1H-pyrimidine-2,4-dione with (8S, 9R) configuration of the alkaloid moiety was obtained with 62% yield.

$^1$H NMR (300/400 MHz, DMSO-d$_6$): δ 1.18 (t, 1H), 1.23 (s, 1H), 1.56 (m, 1H), 1.70 (m, 1H), 1.79 (s, 1H), 2.13 (m, 1H), 2.21 (m, 1H), 2.29 (s, 1H), 2.73 (s, 1H), 3.07 (m, 1H), 3.17 (s, 1H), 3.39 (d, 4H, J=2.5 Hz), 3.64 (m, 1H), 4.09 (dt, 1H), 4.26 (m, 1H), 4.48 (m, 1H), 4.69 (m, 1H), 4.95 (d, 3H, J=10.3 Hz), 5.02 (d, 3H, J=17.3 Hz), 5.82 (ddd, 1H, J=17.2, 10, 7.6 Hz), 6.15 (t, 1H, J=6.4 Hz), 7.13 (d, 1H, J=7.8 Hz), 7.50 (d, 1H, J=8.0 Hz), 7.66 (t, 1H, J=7.5 Hz), 7.80 (t, 1H, J=7.2 Hz), 8.15 (s, 1H), 8.42 (d, 1H, J=7.8 Hz), 8.94 (s, 1H), 10.01 (s, 1H);

$^{13}$C NMR (DMSO-d$_6$): δ 8.63, 20.80, 26.91, 37.93, 45.56, 51.26, 59.75, 61.87, 70.68, 84.28, 84.68, 115.26, 123.93, 124.91, 125.23, 125.52, 126.78, 128.10, 129.26, 129.87, 137.76, 139.00, 141.28, 143.18, 145.51, 148.06, 149.02, 150.15, 156.86, 157.12;

$^{19}$F NMR (DMSO-d$_6$): δ −76.35, −166.25; MS ES: m/z (−) 602 (M−H)$^−$, 638/641 (M+Cl)$^−$, 682/684 (M+Br)$^−$; (+) 604 (M+H)$^−$, 626 (M+Na)$^+$.

EXAMPLE 9

Synthesis of Compound PCN5AFU

Using a procedure identical as in Example 2, a reaction between 5AddFU (82 mg; 0.302 mmol) and 9-O-propargylcinchonine (100.4 mg; 0.302 mmol) was performed. Following chromatographic purification, 5-fluoro-1-(4-hydroxy-5-{4-[quinolin-4-yl-(5-vinyl-1-aza-bicyclo[2.2.2]oct-2-yl)-methoxy-methyl]-[1,2,3]triazol-1-ylmethyl}-tetrahydro-furan-2-yl)-1H-pyrimidine-2,4-dione with (8R, 9S) configuration of the alkaloid moiety was obtained with 60% yield.

$^1$H NMR (300/400 MHz, DMSO-$d_6$): δ 1.17 (t, 1H), 1.24 (s, 1H), 1.70 (s, 1H), 2.13 (m, 1H), 2.23 (dd, 1H, J=13.7, 6.8 Hz), 2.29 (s, 2H), 3.17 (s, 1H), 4.08 (dt, 1H), 4.28 (d, 1H, J=2.1 Hz), 4.45 (m, 1H), 4.64 (dd, 1H, J=8.1 Hz), 4.68 (s, 1H), 4.70 (m, 1H), 4.74 (d, 1H, J=4.3 Hz), 4.98 (s, 1H), 5.03 (d, 1H, J=9.0 Hz), 5.58 (s, 1H), 5.86 (ddd, 1H, J=17.2, 10.1, Hz), 6.16 (t, 1H), 7.13 (d, 2H, J=7.8 Hz), 7.50 (d, 1H, J=8), 7.58 (d, 1H, J=4.3 Hz), 7.66 (t, 1H), 7.80 (t, 1H), 7.98 (d, 1H, J=7.0 Hz), 8.08 (d, 1H, J=8.2 Hz), 8.13 (s, 1H), 8.32 (m, 1H), 8.92 (d, 1H, J=4.3 Hz), 10.00 (s, 1H);

$^{13}$C NMR (DMSO-$d_6$): δ 20.83, 27.29, 37.82, 38.17, 47.60, 48.77, 51.29, 62.00, 70.71, 79.21, 84.31, 123.64, 124.92, 125.53, 126.82, 128.14, 129.09, 129.85, 137.81, 139.07, 141.24, 143.56, 145.57, 148.07, 149.06, 150.19, 156.65, 157.22;

$^{19}$F NMR (DMSO-$d_6$): δ −166.16; MS ESI: m/z (−) 603 (M−H)$^-$, 638 (M+Cl)$^-$; (+) 604 (M+H)$^-$.

EXAMPLE 10

Synthesis of PCN5AFU Dihydrochloride

To a round-bottomed flask, PCN5AFU (100 mg; 0.16 mmol) was added; it was dissolved in methanol (3 ml); subsequently, 3 equivalents of HCl as 10% hydrochloric acid solution (0.48 mmol) were added. The solution was stirred at room temperature for 15 minutes; subsequently, the solvent was evaporated in a rotary evaporator on a water bath at 40° C. The dry residue was evaporated twice with methanol (3 mL portion each) to remove any excess HCl. 5-Fluoro-1-(4-hydroxy-5-{4-[quinolin-4-yl-(5-vinyl-1-aza-bicyclo[2.2.2]oct-2-yl)-methoxymethyl]-[1,2,3]triazol-1-ylmethyl}-tetrahydrofuran-2-yl)-1H-pyrimidine-2,4-dione dihydrochloride with (8R,9S) configuration of the alkaloid moiety was obtained as pale yellow, solidifying oil with quantitative yield.

$^1$H NMR (300/400 MHz, CD$_3$OD): δ 1.01 (m, 1H), 1.31 (m, 1H), 2.02 (m, 1H), 2.30 (m, 1H), 2.42 (s, 1H), 2.73 (d, 1H, J=7.9 Hz), 3.13 (m, 1H), 3.50 (m, 1H), 3.65 (s, 1H), 3.76 (s, 1H), 3.97 (m, 1H), 4.21 (m, 1H), 4.40 (m, 1H), 4.64 (d, 1H, J=8.4 Hz), 4.68 (d, 1H, J=8.4 Hz), 4.81 (d, 1H, J=8.4 Hz), 5.13 (m, 1H), 5.90 (ddd, 1H, J=17.2, 10.1, 7.4 Hz), 6.19 (t, 1H, J=6.5 Hz), 6.45 (s, 1H), 7.24 (m, 1H), 7.41 (m, 1H), 7.36 (m, 1H), 7.71 (d, 1H, J=6.7 Hz), 8.13 (s, 1H), 8.25 (m, 1H), 8.31 (m, 1H), 8.74 (d, 1H, J=8.7 Hz), 9.25 (d, 1H, J=5.6).

$^{13}$C NMR (CD$_3$OD): δ 23.77, 28.48, 30.76, 37.97, 39.39, 53.00, 60.97, 63.77, 72.57, 85.79, 87.26, 117.83, 122.64, 126.10, 127.96, 132.30, 136.41, 137.74, 145.87, 156.06.

MS (m/z): (−) 641 (corresponds to the molecular weight of the product less one chlorine atom (M−Cl)$^-$); (+) 604 (corresponds to the molecular weight of the monoprotonated product less two chlorine atoms (M+H)$^-$+); 626 (M+Na)$^+$.

The invention claimed is:
1. 2',5'-Dideoxy-5-fluorouridine derivatives of general formula 1

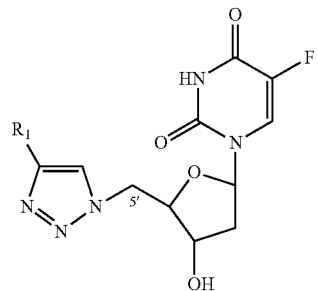

(1)

wherein $R_1$ denotes the group of general formula 2 or 3

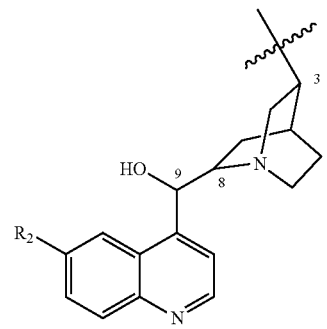

(2)

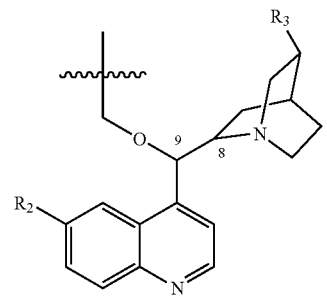

(3)

wherein:
$R_2$ denotes hydroxy group, H or an alkoxy group containing from 1 to 12 C atoms in a straight or branched chain or a cycloalkyl substituent containing from 3 to 10 carbon atoms,
$R_3$ denotes vinyl, ethyl or acetylene group.
2. A process for the manufacture of 2',5'-dideoxy-5-fluorouridine derivatives of general formula 1

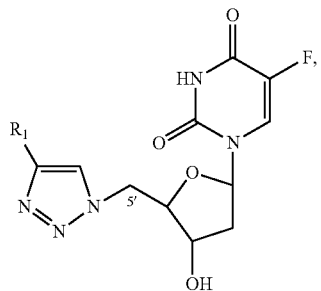

(1)

wherein R₁, R₂ and R₃ are as defined in claim 1, wherein the process comprises a cycloaddition between 5'-azido-2',5'-dideoxy-5-fluorouridine of general formula 11

(11)

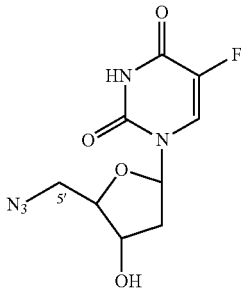

and an appropriate alkyne derivative of a *cinchona* alkaloid of general formula 12 or 13, (12)

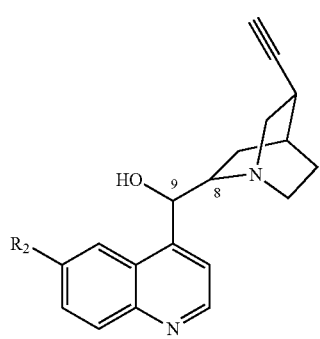

(13)

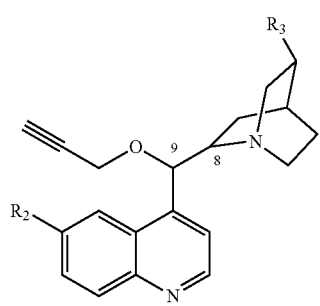

wherein R₂ and R₃ are as defined hereinabove, in the presence of copper(I) ions.

3. Salts of 2',5'-dideoxy-5-fluorouridine derivatives, comprising:
monosalts of general formula 4 or, or
disalts of general formula 6, wherein a double protonated alkaloid fragment is the dication (4)

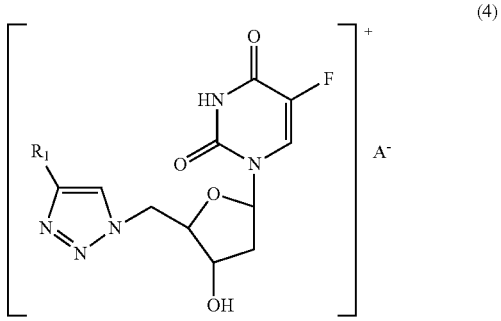

(5)

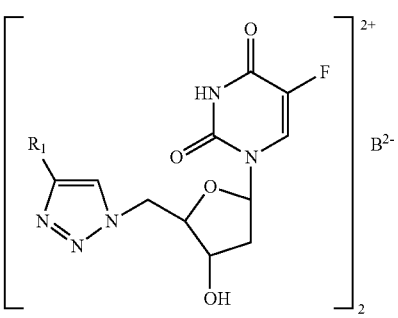

(6)

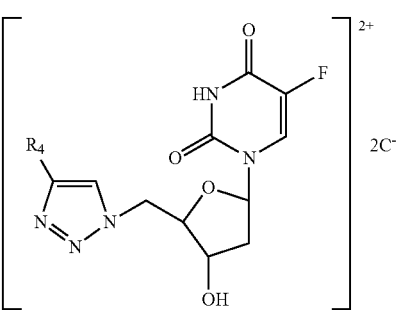

wherein:
A⁻ denotes Cl⁻, Br⁻, I⁻, NO₃⁻, HCOO⁻, CH₃COO⁻, CH₃SO₃⁻, CH₃C₆H₄SO₃⁻, CH₃CH(OH)COO⁻, HOOC(CHOH)₂COO⁻, HOOC(CH₂)₂COO⁻, cis-C₄H₃O₄⁻, trans-C₄H₃O₄⁻, HOCH₂(CHOH)₄COO⁻, C₆H₈O₆⁻, or C₆H₇O₇⁻, B²⁻ denotes SO₄²⁻, HPO₄²⁻, ⁻OOC(CH₂)₂COO⁻, ⁻OOC(CHOH)₂COO⁻, cis-C₄H₂O₄²⁻, or trans-C₄H₂O₄²⁻, C⁻ denotes Cl⁻, Br⁻, I⁻, NO₃⁻, or CH₃SO₃⁻, R₁ denotes a monocation of a fragment of Cinchona alkaloid of natural origin obtained from bark or other parts of *Cinchona* species plants or synthetic of general formula 7 or 8 and with defined absolute configuration at C-8 and C-9 atoms which includes all four possible diastereomeric forms, that is (8R,9S) or (8S,9R) or (8R,9R) or (8S,9S)

(7)

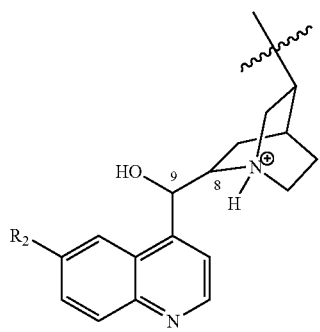

(8)

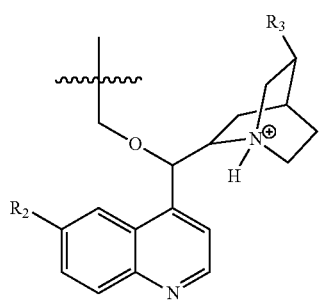

wherein:

R₂ denotes hydroxy group, H or an alkoxy group containing between 1 and 12 C atoms in a straight or branched chain or a cycloalkyl substituent containing between 3 and 10 C atoms, preferably methoxy group, R₃ denotes vinyl, ethyl or acetylene group, R₄ denotes double protonated dication of a fragment of a Cinchona alkaloid of natural origin obtained from bark or other parts of *Cinchona* species plants or synthetic of general formula 9 or 10 and with defined absolute configuration at C-8 and C-9 atoms which includes all four possible diastereomeric forms (8R,9S) or (8S,9R) or (8R,9R) or (8S,9S)

(9)

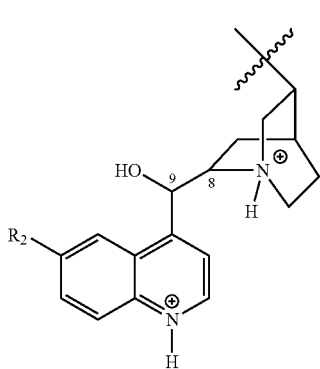

(10)

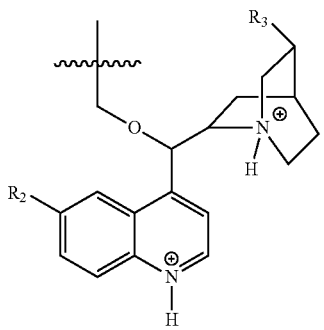

wherein:

R₂ and R₃ are as defined above, and wherein R₄ forms in a reaction of a strop monoprotic acid in a quantity higher than one equivalent with a starting compound of general formula 1

(1)

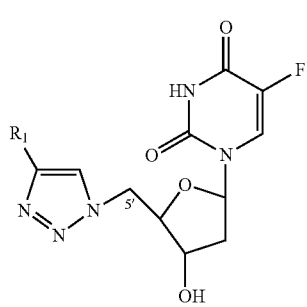

4. A method for treating breast cancer cervical cancer, lung cancer or nasopharynx cancer, comprising administering to a patient in need of treatment for breast cancer, cervical cancer, lung cancer or nasopharynx cancer 2',5'-dideoxy-5-fluorouridine derivatives of general formula 1

(1)

wherein R₁ is the group of general formula 2 or 3

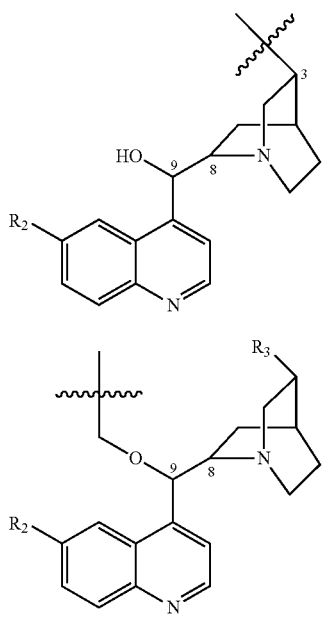

wherein:
R₂ denotes hydroxy group, H or an alkoxy group containing from 1 to 12 C atoms in a straight or branched chain or a cycloalkyl substituent containing from 3 to 10,
R₃ denotes vinyl, ethyl or acetylene group,
and their pharmaceutically acceptable salts.

5. The method according to claim 4, wherein the method is for treating breast cancer, comprising administering to a patient in need of treatment for breast cancer a compound selected from the group consisting of 5 fluoro-1-(4-hydroxy-5-{4-[6-(hydroxy-quinolin-4-yl-methyl)-1-aza-bicyclo[2.2.2]oct-3-yl]-[1,2,3]triazol-1-ylmethyl}-tetrahydro-furan-2-yl)-1H-pyrimidine-2,4-dione with (8R,9S) configuration of the alkaloid moiety, 5-fluoro-1-(4-hydroxy-5-{4-[quinolin-4-yl-(5-vinyl-1-aza-bicyclo[2.2.2]oct-2-yl)-methoxymethyl]-[1,2,3]triazol-1-ylmethyl}-tetrahydro-furan-2-yl)-1H-pyrimidine-2,4-dione with (8R,9S) configuration of the alkaloid moiety, and their pharmaceutically acceptable salts.

6. The method according to claim 4, wherein the method is for treating cervical cancer, comprising administering to a patient in need of treatment for cervical cancer a compound selected from the group consisting of 5-fluoro-1-(4-hydroxy-5-{4-[6-(hydroxy-quinolin-4-yl-methyl)-1-aza-bicyclo[2.2.2]oct-3-yl]-[1,2,3]triazol-1-ylmethyl}-tetrahydro-furan-2-yl)-1H-pyrimidine-2,4-dione with (8R,9S) configuration of the alkaloid moiety, 5-fluoro-1-(4-hydroxy-5-{4-[quinolin-4-yl-(5-vinyl-1-aza-bicyclo[2.2.2]oct-2-yl)-methoxymethyl]-[1,2,3]triazol-1-ylmethyl}-tetrahydro-furan-2-yl)-1H-pyrimidine-2,4-dione with (8R,9S) configuration of the alkaloid moiety, and their pharmaceutically acceptable salts.

7. The method according to claim 4, wherein the method is for treating lung cancer, comprising administering to a patient in need of treatment for lung cancer a compound selected from the group consisting of 5-fluoro-1-(4-hydroxy-5-{4-[6-(hydroxy-quinolin-4-yl-methyl)-1-aza-bicyclo[2.2.2]oct-3-yl]-[1,2,3]triazol-1-ylmethyl}-tetrahydro-furan-2-yl)-1H-pyrimidine-2,4-dione with (8R,9S) configuration of the alkaloid moiety, 5-fluoro-1-(4-hydroxy-5-{4-[quinolin-4-yl-(5-vinyl-1-aza-bicyclo[2.2.2]oct-2-yl)-methoxymethyl]-[1,2,3]triazol-1-ylmethyl}-tetrahydro-furan-2-yl)-1H-pyrimidine-2,4-dione with (8R,9S) configuration of the alkaloid moiety, and their pharmaceutically acceptable salts.

8. The method according to claim 4, wherein the method is for treating nasopharynx cancer, comprising administering to a patient in need of treatment for nasopharynx cancer a compound selected from the group consisting of 5 fluoro-1-(4-hydroxy-5-{4-[6-(hydroxy-quinolin-4-yl-methyl)-1-aza-bicyclo[2.2.2]oct-3-yl]-[1,2,3]triazol-1-ylmethyl}-tetrahydro-furan-2-yl)-1H-pyrimidine-2,4-dione with (8R,9S) configuration of the alkaloid moiety, or 5-fluoro-1-(4-hydroxy-5-{4-[quinolin-4-yl-(5-vinyl-1-aza-bicyclo[2.2.2]oct-2-yl)-methoxymethyl]-[1,2,3]triazol-1-ylmethyl}-tetrahydro-furan-2-yl)-1H-pyrimidine-2,4-dione with (8R,9S) configuration of the alkaloid moiety, and their pharmaceutically acceptable salts.

9. The 2',5'-Dideoxy-5-fluorouridine derivatives derivatives according to claim 1, wherein R₂ denotes methoxy group.

10. The process according to claim 2, wherein R₂ denotes methoxy group.

11. The salts according to claim 3, wherein R₂ denotes methoxy group.

12. The method according to claim 4, wherein R₂ denotes methoxy group.

* * * * *